(12) United States Patent
Adamson et al.

(10) Patent No.: US 6,974,794 B1
(45) Date of Patent: Dec. 13, 2005

(54) HEMOGLOBIN-ANTIOXIDANT CONJUGATES

(75) Inventors: James Gordon Adamson, Georgetwon (CA); Greg Angus McIntosh, Scarborough (CA)

(73) Assignee: Hemosol LP, Mississauga (CA)

( * ) Notice: Subject to any disclaimer, the term of this patent is extended or adjusted under 35 U.S.C. 154(b) by 0 days.

(21) Appl. No.: 09/926,167

(22) PCT Filed: Mar. 20, 2000

(86) PCT No.: PCT/CA00/00299

§ 371 (c)(1),
(2), (4) Date: Jan. 8, 2002

(87) PCT Pub. No.: WO00/56367

PCT Pub. Date: Sep. 28, 2000

(30) Foreign Application Priority Data

Mar. 18, 1999 (CA) ............................................ 2266174

(51) Int. Cl.⁷ ........................ A61K 37/14; A61K 31/05; A61K 31/739; C07K 14/805
(52) U.S. Cl. ........................... 514/6; 514/731; 514/734; 514/54
(58) Field of Search ............................... 514/6, 54, 731, 514/734, 1

(56) References Cited

U.S. PATENT DOCUMENTS

| | | | | |
|---|---|---|---|---|
| 4,001,200 A | * | 1/1977 | Bonsen et al. ............... | 530/385 |
| 4,425,334 A | | 1/1984 | Hunt | |
| 4,831,012 A | * | 5/1989 | Estep ............................ | 514/6 |
| 5,099,012 A | | 3/1992 | Mickle et al. | |
| 5,290,919 A | * | 3/1994 | Bucci et al. ................. | 530/385 |
| 5,532,352 A | | 7/1996 | Pliura et al. | |
| 5,606,025 A | * | 2/1997 | D'Agnillo et al. .......... | 530/385 |
| 5,658,879 A | * | 8/1997 | Nho ............................... | 514/6 |
| 5,780,060 A | * | 7/1998 | Levy et al. .................. | 424/489 |
| 5,789,376 A | * | 8/1998 | Hsia ............................. | 514/6 |
| 6,028,066 A | * | 2/2000 | Unger .......................... | 514/180 |

FOREIGN PATENT DOCUMENTS

| | | |
|---|---|---|
| WO | WO 97 00236 | 1/1997 |
| WO | WO 99 56723 | 11/1999 |

OTHER PUBLICATIONS

"Inhibition of Lipid Peroxidation Promoted by Iron(III) and ascorbate", abstract, Archives of Biochemistry and Biophysics, 1992, 297(2), 258–64.*

Database Embase 'Online! Elsevier Science, Publishers, Amsterdam, NL HSIA J.C. et al: "Pharmacokinetic studies in the rat on a o–raffinose polymerized human hemoglobin." Retrieved from STN Database accession No. 92299803 XP002140429 abstract & biomaterials, Artificial Cells, and Immobilization Biotechnology, (1992) 20/2–4 (587–595).

Database Embase 'Online! Elsevier science Publishers, Amsterdam, NL Mordente A. et al., "Antioxidant properties of 2, 3–dimethoxy–5–mthyl–6(10–hydroxydecyl)–1,4–benzoquinone (idebenone)." Retrieved from STN Database accession No. 1998044603 XP002140430 abstract & chemical research in Toxicology, (1998) 11/1 (54–63).

Database Chemabs 'Online! Chemical Abstracts service, Columbus, Ohio, US Chen, Hao et al.: "Protection by vitamin E, selenium, trolox C, ascorbic acid palmitate, acetylcysteine, coenzyme Q, beta–carotene, canthaxanthin, and (+)–catechi against oxidative damage to liver slices measured by oxidized heme proteins" retrieved from STN Database accession No. 121:26809 XP002140431 abstract & free radical Biol. Med. (1994), 16(4), 437–44.

* cited by examiner

Primary Examiner—Christopher S. F. Low
Assistant Examiner—Brian-Yong S. Kwon
(74) Attorney, Agent, or Firm—Bereskin & Parr Micheline Gravelle

(57) ABSTRACT

There are provided biocompatible chemical compositions having oxygen transporting capability and comprising oxygen transporting molecules chemically bound to antioxidants, to form compositions capable of protecting a mammalian body from oxidative damage. An example of a composition according to the invention is hemoglobin covalently coupled to a 6-hydroxy chroman carboxylic acid, such as Trolox.

10 Claims, 4 Drawing Sheets

10% Topload infusion in conscious rat: Heart rate
(Mean±SEM, n=4)

HEMOGLOBIN-ANTIOXIDANT CONJUGATES

This application claims the benefit of and is the National Phase entry of Patent Cooperation Treaty (PCT) application no. PCT/CA00/00299, filed Mar. 20, 2000, and claims the benefit of priority from previously filed Canadian patent application number CA 2,266,174, filed Mar. 18, 1999, all of which are incorporated herein by reference.

FIELD OF THE INVENTION

This invention relates to hemoglobin compositions, and more specifically to hemoglobin-antioxidant compositions for administration to living beings for oxygen-transport purposes and antioxidant therapeutic purposes.

BACKGROUND OF THE INVENTION

The temporary interruption of blood flow to tissue is a necessary step in many surgical procedures, such as cardiac surgery and organ preservation or transplantation, in order to prevent blood loss and to facilitate surgery. Blood vessels can also become blocked during disease events, such as myocardial infarction, thrombotic stroke, embolic vascular occlusions, angina pectoris, and peripheral vascular insufficiency. The lack of blood supply under these circumstances results in ischemia, which is reversed upon reperfusion of the ischemic tissue with blood or another oxygen-carrying solution. While this readmission of oxygen is critical for the continued function of the tissue, it is generally accepted that the newly introduced oxygen contributes to the formation of oxygen-derived free radicals that cause tissue damage. One mechanism by which introduced oxygen is made toxic is by conversion to superoxide by xanthine oxidase. Levels of this enzyme can become increased during the ischemic period. Simultaneously, levels of reducing, detoxifying agents, such as glutathione, are depleted. Tissue damage occuring as a result of these events is known as reperfusion injury, and is known to occur during reperfusion with blood and is anticipated under some circumstances with the use of blood substitutes.

One class of blood substitutes, the hemoglobin-based oxygen carriers (HBOCs), are comprised of chemically modified acellular hemoglobin. Acellular hemoglobin presents an additional source of potentially damaging reactive oxygen species. Hemoglobin in blood is normally contained within the red blood cells of the blood, in which it circulates through the body to fulfil its oxygen-transporting function. Hemoglobin in the red cells binds oxygen as the blood circulates through the lungs, delivers the oxygen to the body tissues and releases it there, for normal metabolic functions. The chemical behavior of hemoglobin in blood is constrained by its presence in the red cells, which also contain many other components such as enzymes which influence the chemical behavior of hemoglobin therein. When hemoglobin is extracted from red cells and purified ready for use as an acellular oxygen-transporter in blood substitute applications, the chemical influence on the hemoglobin of the other red cell components, and vice versa, is lost.

One of these influences relates to oxygen-hemoglobin reactions, and the generation of toxic oxygen species. Oxidation of hemoglobin by liganded oxygen produces met-hemoglobin, in which heme iron is oxidized to the Fe (III) state, and in which the oxygen free radical "superoxide", $O_2-$ is generated. Met-hemoglobin does not have any significant useful function, since it is incapable of binding and transporting oxygen. Superoxide is, however, linked to a number of deleterious effects in the body, such as oxidative damage and injury to vascular components including endothelium and sub-endothelial tissue. In the red blood cell, enzymes are present to convert these toxic oxygen species to harmless by-products. Thus, the met-hemoglobin reductase enzymatic system is present to reduce the met-hemoglobin to hemoglobin. Superoxide dismutase and catalase are present, respectively to convert superoxide to hydrogen peroxide, and to convert hydrogen peroxide to water and molecular oxygen.

Hemoglobin outside the red cell has no such enzymatic reagents at hand to deal with these oxidation by-products. Consequently, the use of acellular hemoglobin as an oxygen-transporter may produce excessive quantities of deleterious oxidation products such as superoxide, arising from oxygen bound or becoming bound to the hemoglobin itself. Likewise, oxygen dissolved in the HBOC solution, or in the admixed blood reintroduced to the ischemic tissue, may result in reactive oxygen species giving rise to reperfusion injury by the mechanisms described above. However, the need to regain oxygen supply is paramount, and overrides the risks associated with reperfusion injury and introduction of oxygen radicals.

It is an object of the present invention to provide a novel hemoglobin composition capable of providing oxygen while overcoming or at least diminishing the above problem.

SUMMARY OF THE INVENTION

The preparation of synthetic or semi-synthetic oxygen transporting substances such as HBOCs offers the opportunity for attachment of ameliorating substances such as selected antioxidants. Accordingly, the present invention provides a chemical composition having oxygen transporting capability and comprising biocompatible oxygen transporting molecules chemically bonded to one or more biocompatible antioxidants selected from: non-enzymatic phenolic compounds, i.e. compounds containing one or more groups of formula:

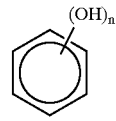

where n is an integer from 1–3, the aromatic ring being further substituted, and being optionally fused or linked to another carbocyclic or heterocyclic ring system; pyrazolines; carotenoid and retinoid compounds; quinones; polypyrroles; indoles and aminoindoles; purine analogs; ascorbic acid; and steroid and alkaloid antioxidants.

Conjugates of the present invention provide the antioxidative functionality in chemically bound proximity to the oxygen transporting molecules. Accordingly, the reactive oxygen species generated by reaction of oxygen-containing solutions are immediately subject to the effects of the antioxidant function, a highly desirable feature since the oxygen species are short lived and do not travel far before causing damage. This is especially important when using HBOCs based on modified hemoglobin, since modified hemoglobins are known to extravasate, and so the antioxidant activity will be transported to any sites to which the HBOC moves. Moreover, the oxidized antioxidant moiety conjugated to the oxygen transporter may be reduced in vivo to a chemical state in which it is capable of further antioxidant activity, and the conjugate recycled in the body for further such action.

BRIEF REFERENCE TO THE DRAWINGS

DESCRIPTION OF THE PREFERRED EMBODIMENTS

Figure 1:
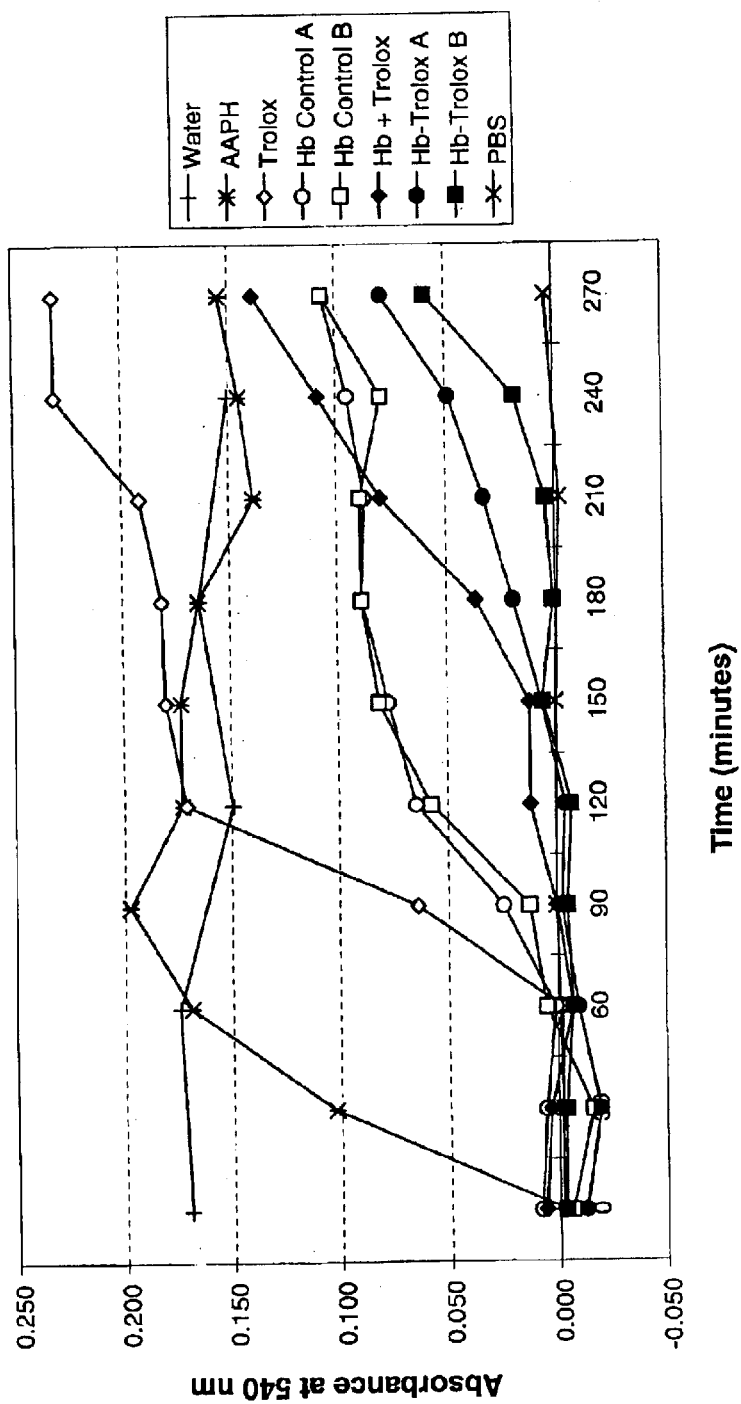
FIGS. 1 and 2 are graphical presentations of the results of Example 2 below.
Figure 2:
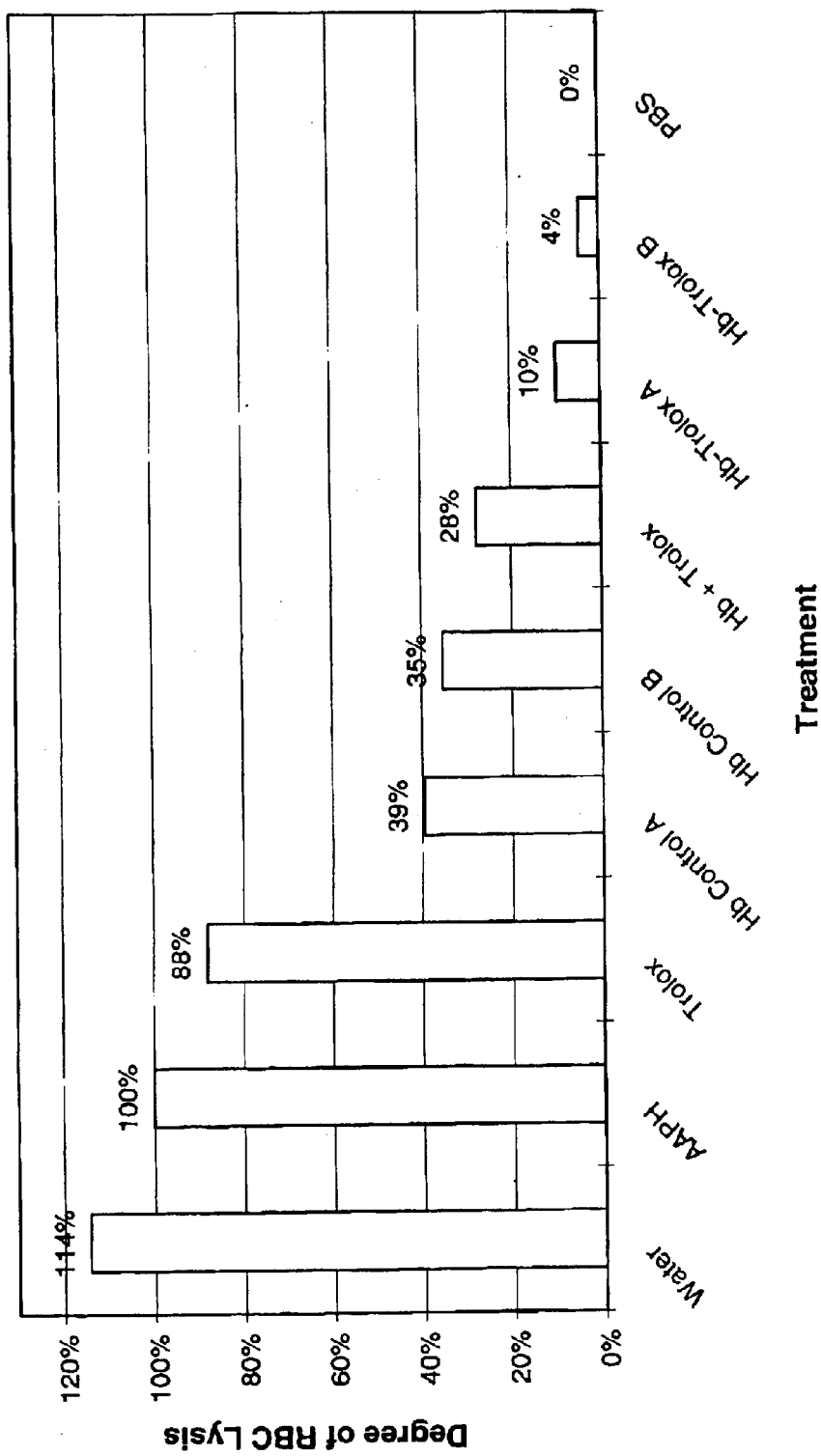

The preferred phenolic compounds for use as antioxidants in the present invention are polyphenolic and substituted phenolic antioxidants such as probucol and esters thereof, bis(1,1-methyl ethyl)-4-[(1-ethylamino]methyl phenol and addition salts thereof, and 5-(3,5-ditert.butyl-4-hydroxybenzyl)thiazolidin-4-one; phenolic ethers such as (3,5-ditert.butyl-4-hydroxyphenylthio) alkanols; di-tert.butylhydroxyphenylthio-substituted hydroxamic acids; chroman-based compounds such as chromanols and dihydrobenzofuranols; flavanoids and isoflavanoids such as flavanone and dihydroflavanol; gallates; catechols and catechol derivatives; and phenolic acids such as p-hydroxybenzoic acid, dihydroxybenzoic acid, and 2-(2,3-dihydro-5-acetoxy-4,6,7-trimethyl)benzofuranyl acetic acid. Especially preferred are the chromanols such as tocol and the tocopherols, and more especially the 6-hydroxy chromans such as 6-hydroxy chroman carboxylic acids and 6-hydroxychroman-2-carbonitriles. Another preferred phenolic compound is 3,4-dihydro-6-hydroxy-2H-1-naphthopyran.

Suitable pyrazolinones are exemplified by norphenazone and 3-methyl-1-phenyl-pyrazolin-5-one.

The preferred caratenoid and retinoid compounds are vitamin A, carotenes, lycopene and lutein.

Preferred among the suitable quinone antioxidant compounds are Coenzyme Q and the various plant-derived quinones such as the plastiquinones.

An example of a preferred tetrapyrrole compound is bilirubin.

Melatonin is an example of a suitable, preferred indole compound for use herein.

Purine analogs useful herein include uric acid, allopurinol and oxypurinol.

Preferred among the suitable steroid antioxidants is methylprednisolone succinate, and lazaroids (21-aminosteroids) such as tirilazad.

The chemistry of conjugation of the biocompatible antioxidant to the oxygen transporting substance is within the skill of the art, based on a consideration of the available chemical groups on the chosen antioxidant and those on the chosen oxygen transporter. Care needs to be taken to ensure that neither the oxygen transport function nor the antioxidant capability is significantly impaired by the chosen form of conjugation.

The oxygen transporting compound can be a heme-protein macromolecule such as hemoglobin or heme-albumin, which transport oxygen by reversible binding of the oxygen to the heme moiety, or a perfluorocarbon, which dissolves gaseous oxygen and delivers it as, a solution. Preferred among the available oxygen transporting compounds is hemoglobin.

The hemoglobin species for use in preferred conjugates of the present invention may be substantially any biocompatible hemoglobin capable of oxygen transport. It may be of human or animal origin. Thus it may be obtained from mammalian red blood cells, e.g. outdated human blood, by lysis of the red cells and separation and purification of the hemoglobin so obtained, by methods known in the art. The resultant hemoglobin should be stroma free and endotoxin free, for best biocompatibility. Alternatively, the hemoglobin may be prepared, in native or mutant form, by recombinant techniques and cell culture techniques known in the art. The use of natural or unnatural mutant hemoglobin species is also within the scope of the invention.

A specific preferred class of oxygen transporter-antioxidant conjugates according to the present invention is a chemical conjugate of an oxygen transporting compound and a 6-hydroxy chroman compound having antioxidant properties and corresponding to the general formula:

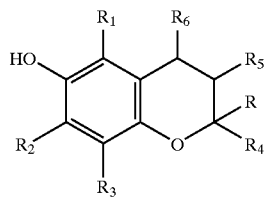

where each of $R_1$, $R_2$ and $R_3$ is independently selected from H, $C_1$–$C_8$ alkyl and $(CH_2)_nX$ where n is an integer from 0 to 20; each of R, $R_4$, $R_5$ and $R_6$ is independently selected from H, $C_{1-20}$ alkyl, X and —$(CH_2)_mX$ where m is an integer from 0–20; and X is a reactive functional group selected in conjunction with the chosen oxygen transporting compound so as to be reactive therewith to effect chemical linkage of the oxygen transporting compound to the chroman compound; with the proviso that the chroman compound includes at least one functional group X.

In such conjugates, the oxygen transporting compound is preferably a heme-protein macromolecule, such as a hemoglobin species, and the functional group X on the chroman is a group capable of being reacted with amino acid residues of the protein chains thereof. Examples of suitable choices for group X are halo, carboxy, amino, hydroxyl, thiol, azide, azo, aldehyde, guanidine and phosphate.

An especially preferred class of conjugates according to the present invention is hemoglobin-chroman-carboxylic acid conjugates, i.e. group X is COOH, chemically covalently bound to the hemoglobin using its carboxyl function. The bonding may be direct, to primary amine groups on the globin chains of hemoglobin. Alternatively an appropriate chemical linker may be used. The chroman-carboxylic acids used in this embodiment of the present invention are in many cases known as bioacceptable antioxidants, capable of scavenging superoxide and other reactive oxygen species formed in vivo. It has been found according to the present invention that the antioxidant function of the chroman-carboxylic acids remains at least substantially unimpaired following conjugation to the hemoglobin species, and in fact appears to be increased by conjugation, over the antioxidant effect of a physical mixture of hemoglobin and the chroman carboxylic acid. The hemoglobin conjugates of the present invention retain oxygen-transporting capability.

A preferred form of hemoglobin species for use in the present invention is cross-linked hemoglobin, in which the tetrameric hemoglobin units have been chemically intramolecularly cross-linked to prevent dissociation into hemoglobin dimers. As is well known, this tendency for dissociation of natural hemoglobin tetramers into dimers is another consequence of extracting hemoglobin from the red cells of blood. Hemoglobin dimers formed by such dissociation, of molecular weight about 32,000 Daltons, are prematurely lost from the system by excretion through the kidney, and so dissociation should be minimized. A variety of methods are known and disclosed in the art for intramolecularly cross-linking hemoglobin to guard against such dissociation, using a variety of chemical cross-linkers such as glutaraldehyde, polyaldehydes such as those derived from oxidative ring opening of sugars and polysaccharides, diaspirin compounds, pyridoxyl compounds, trimesoyl compounds, and the like. The hemoglobin used in the present invention may also be polymerized by intermolecular linking of two or more such tetramers, preferably up to twelve such tetramers, into a polymeric form, using the same or multiple cross-linking reagents. Mixtures containing two or more different such species of intramolecularly cross-linked and intermolecularly linked hemoglobin are particularly desirable.

In an alternative according to the present invention, the chroman-carboxylic acid is coupled to a non-cross-linked hemoglobin, and cross-linking of the conjugate is subsequently undertaken, to form intramolecularly stabilized tetrameric hemoglobin-antioxidant complexes, optionally in admixture with oligomerized or polymerized such complexes. The cross-linking reagent used in such a procedure can be any of those mentioned above, although oxidatively ring-opened raffinose (hereinafter "o-raffinose") is preferred, on account of the desirable product composition which it yields. The conditions of the hemoglobin cross-linking reaction, when conducted after conjugation to the chroman-carboxylic acid antioxidant, are not significantly different from those utilized for cross-linking hemoglobin alone.

Using either strategy, whereby hemoglobin is conjugated to the chroman-carboxylic acid prior to cross-linking of the hemoglobin, or cross-linked hemoglobin is conjugated to the chroman-carboxylic acid, any non-crosslinked hemoglobin may be modified with the chroman-carboxylic acid. This is beneficial since the non-cross-linked hemoglobin is still capable of generating reactive oxygen species to which an oxygen scavenging effect should be applied, and this non-cross-linked form of hemoglobin is known to have different biodistribution properties in comparison with cross-linked hemoglobins. Known methods for removal of non-cross-linked hemoglobin can also be used to control the amount of such species.

The present invention can also be used with other modified forms of hemoglobin, such as hemoglobin conjugated to polymers, e.g. appropriately functionalized polyethylene oxide (PEG), polysaccharides, polyamino acids, proteins and insoluble supports, and encapsulated hemoglobin. All can benefit from the presence of antioxidant molecules bonded thereto, as described herein.

The chroman-carboxylic acid used in conjugates of the present invention and corresponding to the above chemical formula may be a vitamin E carboxylic acid derivative, e.g. one in which radical R is a branched alkyl chain of 16 carbon atoms, such as 4,8,12-trimethyl-tridecyl or 4,8,12-trimethyl-3,7-11-tridecatrienyl, with any of the various possible stereoconfigurations. Compounds in which at least one of $R_1$, $R_2$ and $R_3$ is methyl, and $R_4$ is a direct bond are preferred. Another preferred group of compounds is those of the above formula in which R represents methyl.

Most preferred among chroman-carboxylic acids for use in the present invention is 2,5,7,8-tetramethyl-2-carboxy-chroman-6-ol, commonly known as Trolox, of chemical formula:

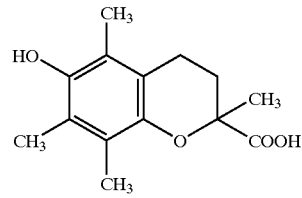

The invention will accordingly be further described with specific reference to the use of Trolox, for ease of description, but this should not be construed as a limitation. Trolox, a vitamin E analog with water solubility greater than that of vitamin E, has antioxidant activity. In accordance with this aspect of the invention, it has been found that conjugation of Trolox to hemoglobin increases the solubility of the Trolox, to achieve higher effective concentrations than possible with free Trolox, to lead to a greater antioxidative effect thereof. The in vivo circulatory half-life of the Trolox is also significantly increased as a result of increasing its mass through conjugation.

Trolox and hemoglobin of any of the aforementioned types can be chemically bonded together. The carboxyl function of the Trolox residue, through appropriate activation, reacts with a primary amine group on a globin chain of hemoglobin, e.g. a lysine residue, to form a covalent amide bond.

The reaction of Trolox and the hemoglobin may be facilitated by the use of an activating chemical compound such as 1-(3-dimethylaminopropyl)-3-ethyl carbodiimide hydrochloride (EDC) or other carbodiimides (alone or in combination with other activators such as N-hydroxysulfosuccinimide), isoxazolium derivatives such as Woodward's reagent K, chloroformates, N,N'-carbonyldiimidazole, N-carbalkoxydihydroquinolines and the like. The Trolox may be used in acid, acid derivative or symmetrical anhydride form. Activating compounds such as EDC react first with the Trolox to activate the Trolox carboxyl group, which then reacts with an amino group of hemoglobin, with elimination of the EDC functionality. The use of such activating compounds allows for larger loadings of Trolox onto hemoglobin, and better control over the amount of such loading. Various solvents can be used as necessary in combination with the aqueous hemoglobin solution to aid solubility of the Trolox and the coupling reagents.

The conditions and procedures for reacting hemoglobin which such carbodiimide compounds are well within the skill of the art. Reactions suitably take place at room temperatures, using aqueous solutions.

Instead of direct bonding, a chemical spacer or linker may be utilized, so that the conjugate comprises hemoglobin to which one or more non-Trolox molecules are bonded, and Trolox is bonded to the non-Trolox chemical residues. Examples of such linkers include functionalized sugars and polysaccharides, polyamino acids such as polylysine, PEG derivatives, and various bi- or polyfunctional linkers. The use of such linkers can provide several Trolox attachment sites per bond to hemoglobin, to provide greater loading with Trolox with less modification of the hemoglobin. It also allows various modifications to the properties of the conjugates (solubility, activity, etc.) by choice of appropriate linker.

The precise group or groups on the globin chains which are used to bind to the Trolox, optionally through the linker, do not appear to be critical. The sites may be on either or both of the alpha globin chains and the beta globin chains. For chemical linking purposes, one can use not only the amino groups but also other functional groups such as thiol, carboxylate, guanidino, imidazole or hydroxyl, of the hemoglobin species, with appropriate choice of linkers and their applicable chemistry. Such choices are within the skill of the art.

A preferred feature of the process of the invention is the addition of the desired quantity of Trolox in several sequential aliquots, e.g. 2–5, instead of as a single addition of the entire amount. Such sequential addition was demonstrated to increase loading of Trolox onto hemoglobin, and to resultant products with greater antioxidant activity.

The preferred amount of Trolox conjugated to hemoglobin according to the present invention is determined on the basis of providing sufficient Trolox to perform its antioxidant, radical scavenging function in practice, but not so much as to interfere with the oxygen transporting capability and oxygen affinity of the HBOC. The amount can be controlled by control of the amount of activating material and/or Trolox added to the reaction solution in which the conjugate is made. Suitable such relative amounts of hemoglobin and Trolox are from about 1 to about 100, with the most preferred amounts being from about 10 to about 100.

After preparation of the conjugate as described, the product is carefully and thoroughly purified to remove unchanged reagents and any other contaminants, if desired. Purification may be by chromatography (size exclusion, hydrophobic interaction chromatography, affinity, ion exchange, etc.) or other methods known in the art, including dialysis/diafiltration, ultrafiltration, or selective precipitation, centrifugation, extraction or any other form of separation. The conjugate is suitably stored under sealed, non-oxidative conditions, at refrigerator temperatures such as 4° C. or at higher temperatures, as an aqueous solution ready for administration to a patient as required. Alternative storage conditions such as lyophilized powder and frozen solution may also be used.

The invention is further described, for illustrative purposes, in the following non-limiting specific examples:

SPECIFIC DESCRIPTION OF THE MOST PREFERRED EMBODIMENTS

EXAMPLE 1

Preparation and Characterization of Conjugates

A series of experiments was conducted in which Trolox (TX) was conjugated to carbonmonoxyhemoglobin (COHb) using 1-(3-dimethylaminopropyl)-3-ethylcarbodiimide hydrochloride (EDC) as a coupling agent under different conditions set out in Table 1 below. In each case, EDC, EDC and Trolox (TX) were combined in equimolar concentration in acetonitrile for 10 minutes at room temperature to provide a stock TX-EDC solution (1.55 M). The stock TX-EDC solution was diluted with acetonitrile, if necessary, just prior to addition to Hb so that the final acetonitrile and TX-EDC content of the conjugation reaction was as indicated in Table 1. All conjugations were done in 40–50 mM MES buffer at the indicated pH values. Reaction mixtures were held at 22° C. for up to 24 hours under CO gas. Samples were filtered and dialyzed against phosphate-buffered saline (PBS), pH 7.4, prior to analysis.

TABLE 1

Preparation of Trolox-Hb reaction solutions

| Rxn | Trolox (mM) | CO-Hb (mM) | TX:Hb ratio | pH | Time (hr) | Acetonitrile (volume %) |
|---|---|---|---|---|---|---|
| 1 | 1.55 | 1.55 | 1 | 7 | 24 | 10 |
| 2 | 1.55 | 0.155 | 10 | 7 | 24 | 10 |
| 3 | 15.5 | 1.55 | 10 | 7 | 24 | 10 |
| 4* | 15.5 | 0.155 | 100 | 7 | 24 | 10 |
| 5* | 155 | 1.55 | 100 | 7 | 24 | 10 |
| 6 | 155 | 1.55 | 100 | 7 | 20 | 10 |
| 7 | 15.5 | 0.155 | 100 | 7 | 20 | 1 |
| 8 | 155 | 1.55 | 100 | 7 | 4 | 10 |
| 9 | 155 | 1.55 | 100 | 6 | 4 | 10 |

For characterization of the conjugates so prepared, reverse phase HPLC was used to separate the globin chains (native or modified) of conjugates. Heme is also separated during this process. Electrospray mass spectrometry coupled to reverse phase HPLC (LCMS) was used to determine molecular weights of the chains (Table 2). Typically, modified chains eluted later than unmodified chains. Three major modified chains were identified by LCMS (Table 3): beta chain with one Trolox molecule attached ($\beta(TX)_1$), and alpha chains with one ($\alpha(TX)_1$) or two ($\alpha(TX)_2$) Trolox molecules attached. Masses are in agreement with amide-linked conjugates. Control reactions, in which Hb was treated with acetonitrile alone, showed no evidence of globin chain modification.

Examination of the globin chain modification data reveals the control afforded by appropriate manipulation of the reaction conditions. The ratio of TX to hemoglobin during the conjugation has the greatest effect on globin chain modification. Increasing TX:Hb ratio from 1:1 to 10:1 to 100:1 at 1.55 mM Hb increased globin chain modification from 1.5 to 24.0 to 50.5% in reactions 1, 3 and 5, respectively. At 0.155 mM Rb, increasing the TX:Hb ratio from 10:1 to 100:1 increased globin chain modification from 22.0 to 79.5% in reactions 2 and 4, respectively. Increasing reactant concentration had little effect using a TX:Hb ratio of 10:1, yielding 22.0 and 24.0% chain modification at 0.155 and 1.55 mM Rb in reactions 2 and 3, respectively. Globin modification was lowered (79.5 to 50.5%) by increasing Hb concentration from 0.155 to 1.55 mM at 100:1 TX:Hb. A 10-fold dilution of all reactants, holding TX:Hb constant at 100:1, resulted in a minor decrease in globin modification (reactions 6 vs. 7), as did shorter reaction time (reactions 5 vs. 8), and increasing pH from 6 to 7 (reactions 8 vs. 9). Lowering acetonitrile content from 10 to 1% (v/v) resulted in globin modifications of 79.5 and 59.4% in reactions 5 and 8, respectively.

TABLE 2

Distribution of modified globin chains under various TX-EDC reaction conditions.

| Rxn | Modified chains (%) | $\alpha (TX)_1$ (%) | $\alpha (TX)_2$ (%) | $\beta (TX)_1$ (%) | Other (%) | Conjugated TX:Hb ratio* |
|---|---|---|---|---|---|---|
| 1 | 1.5 | 1.5 | 0.0 | 0.0 | 0.0 | 0.1 |
| 2 | 22.0 | 13.9 | 1.1 | 4.0 | 3.1 | 0.8 |
| 3 | 24.0 | 12.4 | 0.0 | 6.0 | 5.6 | 0.7 |
| 4 | 79.5 | 26.3 | 21.0 | 24.5 | 7.6 | 3.7 |
| 5 | 50.5 | 32.8 | 4.7 | 4.8 | 8.2 | 1.9 |
| 6 | 66.7 | 35.6 | 7.0 | 11.5 | 12.6 | 2.4 |
| 7 | 59.4 | 25.3 | 3.9 | 10.4 | 19.8 | 1.7 |

TABLE 2-continued

Distribution of modified globin chains under various TX-EDC reaction conditions.

| Rxn | Modified chains (%) | α (TX)$_1$ (%) | α (TX)$_2$ (%) | β (TX)$_1$ (%) | Other (%) | Conjugated TX:Hb ratio* |
|---|---|---|---|---|---|---|
| 8 | 43.7 | 26.4 | 3.9 | 5.4 | 7.9 | 1.6 |
| 9 | 52.6 | 33.6 | 3.6 | 8.2 | 7.2 | 2.0 |

*Conjugated TX:Hb ratio does not include uncharacterized species listed as other.

TABLE 3

Calculated and observed masses for globin chains of Hb-TX conjugates

| Globin chain | Calculated mass (Da) | Observed mass (Da) |
|---|---|---|
| α | 15126 | 15125 |
| β | 15868 | 15864 |
| α(TX)$_1$ | 15358 | 15358 |
| α(TX)$_2$ | 15591 | 15595 |
| α(TX)$_1$ | 16100 | 16099 |

EXAMPLE 2

Measurement of Antioxidant Activity

Blood was collected into heparinized tubes and erythrocytes were separated by centrifugation and washed 3 times with 10 volumes of PBS, pH 7.4. During the last washing, erythrocytes were centrifuged at 1000×g for 10 minutes to obtain a consistently packed cell preparation. The assay for hemolysis mediated by peroxyl radicals was conducted by a modified method of Miki et al.,(M. Miki, H. Tamai, M. Mino, Y. Yamamoto and E. Niki., *Arch. Biochem. Biophys.* 258:373–380 (1987)). Equal volumes of a 30% suspension of fresh erythrocytes in PBS pH 7.4, test sample, and 300 mM 2,2;-azo-bis(2-amidinopropane dihydrochloride) (AAPH, a radical generator) were combined in order. Mixtures were prepared under CO gas and test hemoglobin concentration in the RBC assay suspension was 12–13 mg/ml. Mixtures were held at 37° C., and aliquots were diluted 20-fold in PBS and centrifuged at 1000×g for 10 minutes. As a measure of Hb released due to RBC lysis, the absorbances of supernatants were measured at 540 nm after conversion of all Hb to CN-metHb according to the method of Tentori (Meth. Enzymology 75:707 (1981)). Supernatant Hb levels were corrected for Hb added in the test samples.

The results for two products are presented graphically in FIG. 1, a plot of relative RBC lysis against time for the various products. Products analyzed were prepared as described for reaction #6 (Hb-Trolox B) and reaction #7 (Hb-Trolox A) in Table 1 of Example 1. In the absence of conjugate (AAPH only), RBC lysis is evidenced by increasing levels of Hb in supernatant over the incubation period. Supernatant Hb levels do not increase to the same level over this period in test mixtures containing Hb-Trolox conjugates, indicating protection against the lytic effect of the radical generator. Relative protection was also determined by comparison of areas under the curves (AUC) obtained by plotting RBC lysate absorbance versus time. AUC is determined by the time of onset, rate, and overall extend of RBC lysis. Lower AUC values indicate greater protection of RBCs against lysis. AUCs for Hb-Trolox A and B were significantly lower than for products from corresponding control reactions (no TX-EDC added, Table 4).

TABLE 4

Degree of antioxidant protection by Hb-Trolox conjugates and controls.

| Sample | Trolox (TX) concentration (mM) | Hemoglobin concentration (mN) | AUC relative to AAPH control (%) |
|---|---|---|---|
| AAPH | 0 | 0 | 100 |
| Free Trolox | 0.50 | 0 | 88 |
| Free Hb (A) | 0 | 0.20 | 39 |
| Free Hb (B) | 0 | 0.20 | 35 |
| Free TX + Hb | 0.50 | 0.20 | 28 |
| Hb-Trolox A | 0.32 | 0.20 | 10 |
| Hb-Trolox B | 0.45 | 0.20 | 4 |
| PBS | 0 | 0 | 0 |

AUC data for RBC lysis in the presence of free Trolox, free (control) hemoglobin, and a mixture of free Trolox and hemoglobin is also shown. Both the Trolox and hemoglobin, alone, show less protection than the corresponding hemoglobin-Trolox conjugates containing the same amount of hemoglobin and the same or lower concentration of Trolox in bound form. The mixture of the free Trolox and hemoglobin shows greater protection than an equal concentration of either compound alone, but still less protection than the corresponding hemoglobin-Trolox conjugates containing the same amount of hemoglobin and the same or lower concentration of Trolox in bound form. Since the conjugate and the mixture have the same hemoglobin content, and the conjugate contains the same or less Trolox than the mixture, then the greater activity of the conjugate suggests a synergistic effect, indicated by an increase in overall antioxidant activity due to conjugation.

EXAMPLE 3

Polymerization of Hemoglobin Modified with Trolox

Hemoglobin-Trolox conjugates (Hb-Trolox A and B) prepared in Example 1 were dialyzed against 50 mM Bis-Tris buffer, pH 6.8. Three equivalents o-raffinose (U.S. Pat. No. 5,532,352 Pliura et. al.) dissolved in water were added to solutions of hemoglobin-Trolox to give a final hemoglobin concentration of 42 mg/mL. The mixtures were held under CO gas at 22° C. for 24 hours. The solutions were made 30 mM in sodium acetate, and 20 equivalents of aqueous dimethylamine borane relative to o-raffinose content were added. After 24 hours, the solutions were dialyzed against water then PBS pH 7.4. Size exclusion chromatography under dissociating, non-denaturing conditions indicated formation of intra- and intermolecularly cross-linked hemoglobin-Trolox species (Table 5). Hb-Trolox not cross-linked by o-raffinose elutes as 32 kDa alpha-beta globin dimers under the chromatography conditions used. This non-cross-linked Hb species can be removed if necessary by conventional means such as ultrafiltration or chromatography. Optimization of conditions to control the amount of non-cross-linked Hb species is possible.

TABLE 5

Molecular weight distribution of o-raffinose polymerized hemoglobin-Trolox

| Molecular weight species (kDa) | Molecular weight distribution (%) | |
|---|---|---|
| | Polymerized Hb-Trolox A | Polymerized Hb-Trolox B |
| 32 | 12.2 | 11.8 |
| 64 | 44.7 | 41.1 |
| >64 | 43.1 | 47.1 |

EXAMPLE 4

Trolox-Polymerized Hb Conjugate Preparation

Trolox was conjugated to o-raffinose cross-linked Hb (polyOR-Hb, U.S. Pat. No. 5,532,352 Pliura et al.) Using the method of Example 1. A 100-fold molar excess of TX-EDC was reacted with polyOR-Hb in 100:mM MES buffer at pH 5,6 and 7. All samples were analyzed by size exclusion chromatography (SEC) and reversed phase HPLC (RP HPLC). In polyOR-Hb, alpha and beta chains are 33 and 90% modified by o-raffinose, respectively, prior to reaction with TX-EDC (Table 6). After reaction with TX-EDC at three different pH values, alpha and beta chain modification was increased to 67–77% and 93–99%, respectively, and several new modified chains were observed by RP HPLC. Some of these TX-modified chains corresponded to those observed after reaction of Hb with TX-EDC, as identified in Example 1.

TABLE 6

Modification of globin chains of polyOR-Hb-TX conjugates

| Rxn | Sample | Rxn pH | % Modification of Globin compared to Hb | | Increase in % Modification of Globin Compared to polyOR-Hb | |
|---|---|---|---|---|---|---|
| | | | Beta | Alpha | Beta | Alpha |
| 1 | Hb | n/a | n/a | n/a | n/a | n/a |
| 2* | polyOR-Hb | n/a | 90.2 | 33.3 | n/a | n/a |
| 3 | polyOR-Hb-TX | 7 | 93.4 | 75.6 | 3.2 | 42.3 |
| 4 | polyOR-Hb-TX | 6 | 99.7 | 77.1 | 9.5 | 43.8 |
| 5 | polyOR-Hb-TX | 5 | 96.6 | 67.3 | 6.4 | 34 |

*Control reaction, no Trolox or EDC added.

EXAMPLE 5 i) Conjugation of Trolox to o-raffinose Polymerized Hemoglobin: Single and Multiple Additions of Trolox o-Raffinose polymerized hemoglobin (polyOR-Hb) was prepared as described in U.S. Pat. No. 5,532,352 Pliura et al. To each of two separate solutions (Reactions A and B) of 0.50 g polyOR-Hb in approximately 50 mL 125 mM MES buffer, pH 7.0 was added 0.194 g Trolox which had been pre-reacted for 10–20 minutes at room temperature with 0.149 g EDC in 1 mL acetonitrile. Identical amounts of Trolox/EDC were added to Reaction B at 5 and 19 hours, for a total of three additions. Reaction A had 1 mL volumes of acetonitrile added at the same times. Both reactions were stirred under CO gas at 22° C. for a total of 27 hours. Samples were analyzed following filtration and dialysis against water, Tris-buffered 0.5 M $MgCl_2$ and phosphate buffered saline pH 7.4. No free Trolox was detectable chromatography. Control products were prepared by reaction with EDC alone with no Trolox added.

ii) In Vitro Protection of RBCs Against Lysis

Using the method described in Example 2, the antioxidant activities of the two conjugates were measured. Samples were CO-ligated and concentration of the conjugates and controls in the RBC assay suspension was 12 mg/mL. Both Trolox conjugates showed greater protection than corresponding controls without Trolox. Protection was greatest in the product obtained after three additions of Trolox, which was shown by reverse phase HPLC analysis to be more extensively modified by Trolox than the product obtained by a single addition of Trolox. AUC for the 3-fold addition product was 3% of control, while AUC of the single addition product was 33% of control. The results are presented in Table 7 below.

TABLE 7

Degree of antioxidant protection by PolyOR-Hb-Tx conjugates and controls

| Sample | AUC relative to AAPH control (%) |
|---|---|
| AAPH | 100 |
| 1× Control | 83 |
| 3× Control | 69 |
| 1× TX-EDC (Reaction A) | 27 |
| 3× TX-EDC (Reaction B) | 2 |
| PBS | 0 |

EXAMPLE 6 i) Large Scale Preparation of Trolox Conjugate of o-raffinose Polymerized Hemoglobin (PolyOR-Hb-TX)

o-Raffinose polymerized hemoglobin (polyOR-Hb) was prepared as described in U.S. Pat. No. 5,532,352 Pliura et al. 4.01 g Trolox was reacted with 3.07 g EDC in 40 mL acetonitrile for 10–20 minutes at room temperature. This solution was added to 18.9 polyOR-Hb in 2 L 126 mM MES buffer, pH 7.0 Identical additions of Trolox/EDC were made after 3.5 and 21 hours, for a total of three additions. The reaction was stirred under CO gas at 22° C. throughout the process. After 26 hours total reaction time, the solution was filtered and diafiltered against water, phosphate-buffered saline, and Ringer's lactate to a final Hb concentration of 77 mg/mL. The pH was adjusted to 7.24 with dilute NaOH during the Ringer's lactate diafiltration. No free Trolox was detectable by chromatography. A portion of the product was oxygenated prior to further analysis.

ii) In Vitro Protection of RBCs Against Lysis

Using the method described in Example 1, the antioxidant activity of the polyOR-Hb-TX was measured. Products tested included oxygen and CO-ligated polyOR-Hb (no treatment with TX or EDC), CO-ligated product reserved prior to oxygenation as described above, and oxygenated product. All products were present in the RBC lysis assay suspension at 11.7 mg/mL. The results are presented in Table 8 below. These results indicate better protection of RBCs against lysis by both the oxygenated and carbonmonoxy forms of Trolox conjugates than by controls.

TABLE 8

Degree of antioxidant protection by PolyOR-Hb-Tx and controls

| Sample | AUC relative to AAPH control (%) |
| --- | --- |
| AAPH | 100 |
| PolyOR-Hb (Oxy form) | 39 |
| PolyOR-Hb (CO form) | 47 |
| PolyOR-Hb-TX (Oxy form) | 15 |
| PolyOR-Hb-TX (CO form) | 6 |
| PBS | 0 |

EXAMPLE 7

Figure 3:
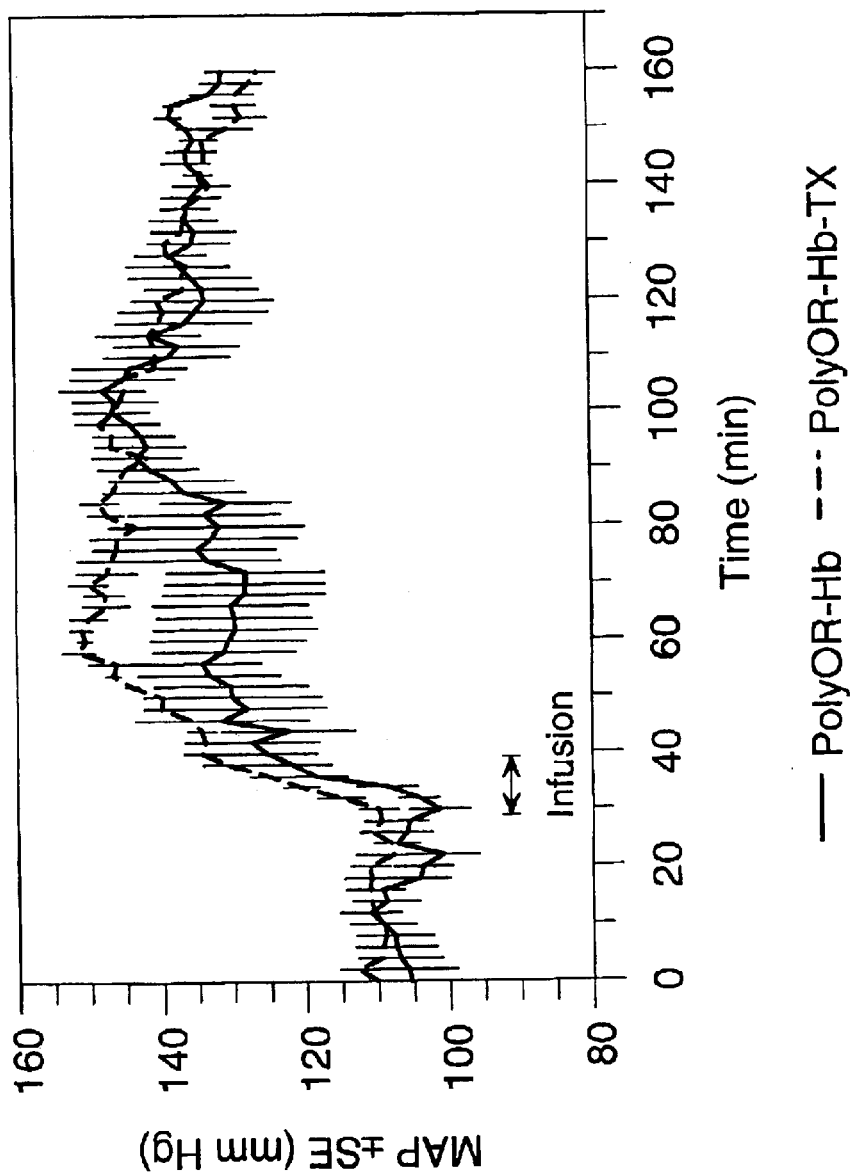
FIGS. 3 and 4 are graphical presentations of the results of Example 7 below.
Figure 4:
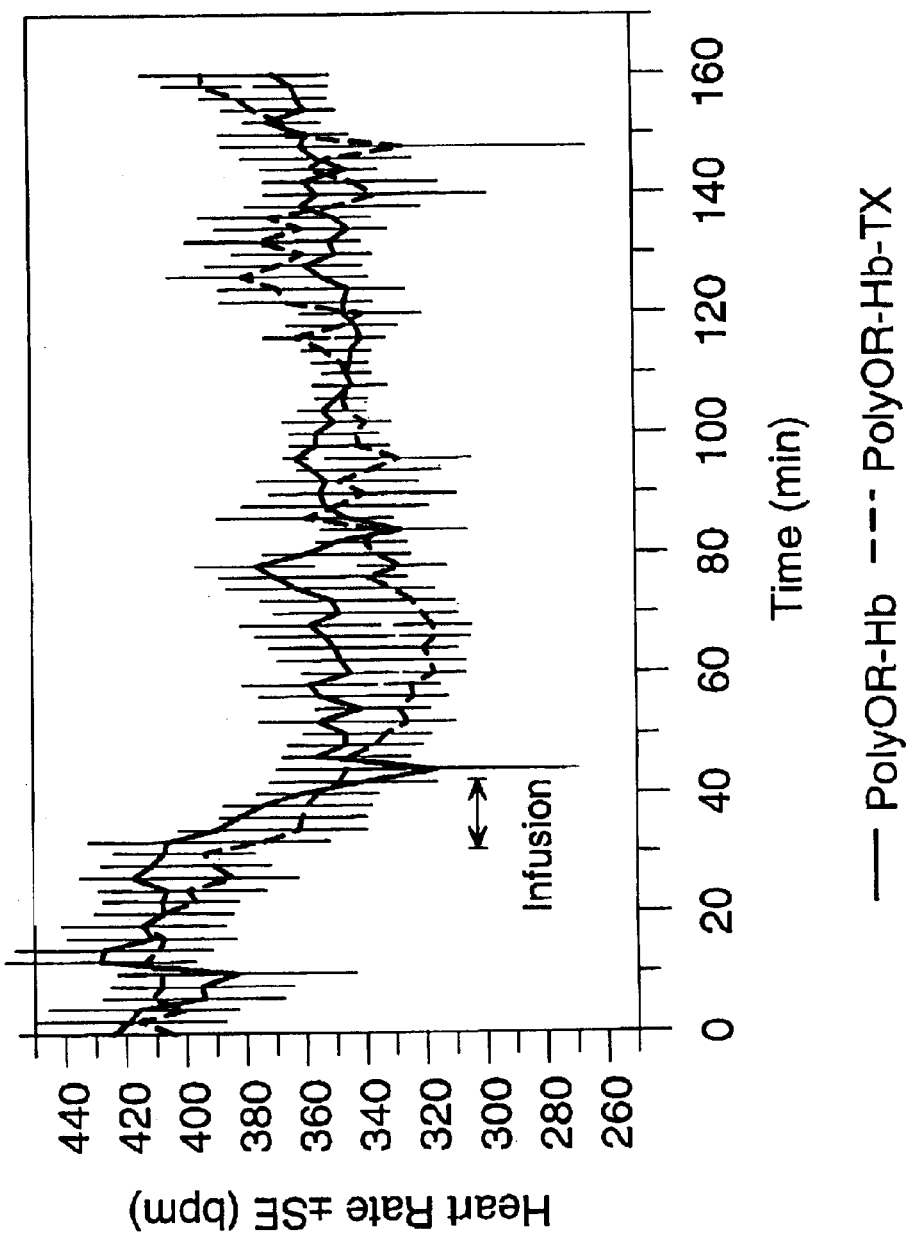

Hemodynamic Effect of polyOR-Hb-TX Following 10% Topload Infusion in Conscious Rat Male Sprague-Dawley rats (250–350 g) were anesthetized with isoflurane on the day of the experiment. The right femoral artery and vein were cannulated. After 1.5 hour recovery from surgery, conscious animals residing in a metabolic cages were infused with either of two solutions: oxygenated polyOR-TX prepared in Example 6 or polyOR-Hb (no TX-EDC treatment; both solutions were 7.7 g/dL in lactated Ringer's solution). Infusion volume was equal to 10% of the animal's estimated blood volume. Mean arterial blood pressure (MAP) and heart rate (HR) were recorded 30 minutes prior to infusion to establish baseline values, during infusion and for 2 hours following infusion (FIGS. 3 and 4). Four animals were tested in each of the two groups. The baseline MAP prior to infusion was 101±4 mm Hg (polyOR-Hb) and 110±3 mm Hg (polyOR-Hb-TX). Following infusion, MAP increased significantly (P<0.01) to 142±7 and 151±1 mm Hg in the polyOR-Hb and polyOR-Hb-TX groups, respectively. The difference in increase was not significantly different between the two groups (P>0.05). Pre-infusion HR were 407±17 and 394±17 beats per minute (bpm) in the polyOR-Hb and polyOR-Hb-TX groups, respectively. HR after infusion decreased significantly (P<0.01) to 345±16 and 316±10 bpm in the polyOR-Hb and polyOR-Hb-TX groups, respectively. The difference in decrease was not significantly different between the two groups (P>0.05). Conjugation of Trolox did not alter the hemodynamic properties of the HBOC polyOR-Hb in this study.

EXAMPLE 8

Conjugation Under Deoxy Conditions

Trolox was conjugated to polyOR-Hb under deoxy conditions to prepare a product with a high $P_{50}$, more suitable for use as an HBOC. PolyOR-Hb and MES buffer were deoxygenated by standard means. 0.78 g Trolox was reacted with 0.60 g EDC in 4 mL of acetonitrile for 10–20 minutes at room temperature. This solution was added to 2.04 g polyOR-Hb in 200 mL 120 mM MES pH 7.0. Two identical additions were made after 4 and 21 hours. At 27 hours following the first addition, the reaction mixture was charged with CO gas, filtered, concentrated and dialyzed extensively against PBS. The $P_{50}$ of the starting polyOR-Hb, the conjugate prepared in this example and the conjugate prepared in Example 6 were found to be 41, 40 and 16 mm Hg respectively, at 37° C., using a Hemox-Analyzer (TCS Instruments, Southampton, Pa., U.S.A).

EXAMPLE 9

Comparison of Antioxidant Activities

Using the method described in Example 1, the antioxidant activities of the polyOR-Hb-TX products prepared under deoxy conditions (Example 8) and CO conditions (Example 6) were measured. Samples were CO-ligated and concentration of the conjugates and controls in the RBC assay suspension was 12 mg/mL. An equal concentration of polyOR-Hb, as well as two concentrations of Trolox alone representing 1× and 0.5× its solubility limit in the test solution, were evaluated. Both conjugates showed greater protection than polyOR-Hb and Trolox controls. This is shown in Table 9 below. Protection was comparable for the products prepared under deoxy and CO conditions.

TABLE 9

| Sample (all Hb-containing samples in CO form) | AUC relative to AAPH control (%) |
| --- | --- |
| AAPH | 100 |
| Trolox (0.26 mM) | 87 |
| Trolox (0.52 mM) | 70 |
| PolyOR-Hb (12 mg/mL) | 28 |
| PolyOR-Hb-TX (from Example 6, 12 mg/mL) | 0 |
| PolyOR-Hb-TX (from Example 8, 12 mg/mL) | 3 |
| PBS | 0 |

What is claimed is:

1. A chemical composition having oxygen transporting capability comprising 2,5,7,8-tetramethyl-2-carboxy-chroman-6-ol (Trolox) conjugate of o-raffinose polymerized hemoglobin (PolyOR-Hb), wherein a ratio of Hemoglobin (Hb) to Trolox during a conjugation is at least 1:1; wherein said composition is prepared by the conjugation of Trolox to o-raffinose polymerized hemoglobin under deoxy or carbon-monoxy condition; and wherein said composition provides greater protection of red blood cells (RBCs) against lysis.

2. The composition of claim 1, wherein the hemoglobin is intramolecularly cross-linked.

3. The composition of claim 2, wherein the hemoglobin is intramolecularly cross-linked with oxidized raffinose.

4. The composition of claim 2, wherein the hemoglobin is intramolecularly and intermolecularly cross-linked.

5. The composition of claim 1, wherein the hemoglobin is deoxyhemoglobin.

6. The composition of claim 1, wherein the hemoglobin is carboxyhemoglobin.

7. The composition of claim 1, wherein the Hb:Trolox ratio is 1:1–1:3.7.

8. The composition of claim 1, wherein the Trolox is conjugated to PolyOR-Hb under the deoxy condition to prepare said composition with a P50 of 41 mm Hg.

9. The composition of claim 1, wherein the Trolox is conjugated to PolyOR-Hb under the deoxy condition to prepare said composition with a P50 of 40 mm Hg.

10. The composition of claim 1, wherein the Trolox is conjugated to PolyOR-Hb under the carbonmonoxy condition to prepare said composition with a P50 of 16 mm Hg.

* * * * *